United States Patent
Baril et al.

(10) Patent No.: US 11,969,190 B2
(45) Date of Patent: Apr. 30, 2024

(54) TRANSVAGINAL OCCLUDER

(71) Applicant: Covidien LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

(*) Notice: Subject to any disclaimer, the term of this patent is extended or adjusted under 35 U.S.C. 154(b) by 816 days.

(21) Appl. No.: 16/822,082

(22) Filed: Mar. 18, 2020

(65) Prior Publication Data
US 2021/0290269 A1 Sep. 23, 2021

(51) Int. Cl.
*A61B 17/42* (2006.01)
*A61B 17/12* (2006.01)
*A61B 17/00* (2006.01)
*A61B 17/34* (2006.01)

(52) U.S. Cl.
CPC .... *A61B 17/4241* (2013.01); *A61B 17/12027* (2013.01); *A61B 17/42* (2013.01); *A61B 2017/00862* (2013.01); *A61B 17/1204* (2013.01); *A61B 2017/1205* (2013.01); *A61B 17/3423* (2013.01); *A61B 2017/3429* (2013.01); *A61B 2017/4216* (2013.01)

(58) Field of Classification Search
CPC .............. A61B 17/42; A61B 17/12027; A61B 2017/00862; A61B 17/4241; A61B 2017/1205; A61B 2017/4216; A61B 17/3423; A61B 2017/3429; A61B 17/1204

See application file for complete search history.

(56) References Cited

U.S. PATENT DOCUMENTS

| | | | | |
|---|---|---|---|---|
| 3,402,710 A | * | 9/1968 | Paleschuck | A61M 39/0606 473/611 |
| 5,634,911 A | * | 6/1997 | Hermann | A61B 17/3423 604/246 |
| 6,110,187 A | | 8/2000 | Donlon | |
| 6,398,758 B1 | | 6/2002 | Jacobsen et al. | |
| 8,550,992 B2 | * | 10/2013 | Kleyman | A61B 17/0218 600/206 |
| 8,876,886 B2 | | 11/2014 | Kaufmann et al. | |
| 9,226,736 B2 | | 1/2016 | Obermiller et al. | |
| 9,566,419 B2 | | 2/2017 | Frigstad et al. | |

(Continued)

FOREIGN PATENT DOCUMENTS

WO 2017004265 A1 1/2017

*Primary Examiner* — Jing Rui Ou
(74) *Attorney, Agent, or Firm* — Carter, DeLuca & Farrell LLP (57) ABSTRACT

A transvaginal occluder includes an elongated housing having proximal and distal portions and an internal cavity defined therebetween configured for selective receipt of a surgical instrument therethrough. The elongated housing includes a first material having a first durometer extending between the proximal and distal portions and defining the internal cavity, the first material including one or more recesses defined therein along the internal cavity. The elongated housing also includes a second material having a second, lower durometer and that extends between the proximal and distal portions, the second material encapsulating a portion of the first material and configured to engage vaginal tissue. The elongated housing also includes a third material having a third, lowest durometer disposed within the one or more recesses that is configured to engage a shaft of the surgical instrument in a fluid tight manner.

18 Claims, 4 Drawing Sheets

(56) References Cited

U.S. PATENT DOCUMENTS

| | | | |
|---|---|---|---|
| 2004/0066008 A1* | 4/2004 | Smith | A61B 17/3462 |
| | | | 277/628 |
| 2005/0096695 A1* | 5/2005 | Olich | A61B 17/3462 |
| | | | 606/213 |
| 2005/0165433 A1* | 7/2005 | Haberland | A61M 39/0606 |
| | | | 606/167 |
| 2006/0015171 A1 | 1/2006 | Armstrong | |
| 2006/0149305 A1* | 7/2006 | Cuevas | A61B 17/3462 |
| | | | 606/191 |
| 2008/0140178 A1 | 6/2008 | Rasmussen et al. | |
| 2009/0254169 A1 | 10/2009 | Spenser et al. | |
| 2011/0282250 A1 | 11/2011 | Fung et al. | |
| 2012/0192872 A1 | 8/2012 | Rudakov et al. | |
| 2012/0232475 A1 | 9/2012 | Averbuch | |
| 2014/0296867 A1* | 10/2014 | Sauer | A61B 17/1204 |
| | | | 606/119 |
| 2014/0336752 A1 | 11/2014 | Ginn et al. | |
| 2015/0005808 A1 | 1/2015 | Chouinard et al. | |
| 2015/0007827 A1 | 1/2015 | Ozdil et al. | |
| 2016/0278784 A1 | 9/2016 | Edmiston et al. | |
| 2017/0190492 A1 | 7/2017 | Bentz | |
| 2018/0177622 A1 | 6/2018 | Chu et al. | |

* cited by examiner

TRANSVAGINAL OCCLUDER

TECHNICAL FIELD

This disclosure relates to surgical instruments, and more particularly, to transvaginal occluders used for laparoscopic surgery.

BACKGROUND

In laparoscopic surgery with an insufflated abdomen, an incision at the top of the vaginal canal (called a colpotomy) can open the pressurized peritoneal cavity to ambient pressure through the vaginal canal if the vaginal passageway is not properly sealed at this point, positive pressure insufflation gas passes rapidly out causing the abdominal wall (ceiling) to collapse and halt the operation. Modern, commercially available transvaginal uterine manipulators typically incorporate a feature to occlude gaseous passage out through the vaginal canal after colpotomy.

One common improvised vaginal occluder involves the use of a compliant, plastic bulb component removed from a sterile bulb syringe. These bulbs are often too large for smaller vaginal canals, leading them to fold into themselves, which causes gas leaks, or they are too small for larger canals so gas simply passes around the bulb.

Several purported proprietary vaginal occlusive devices have been disclosed over the past few years. For example, bullet-shaped devices with a circumferential inflatable balloon have been introduced to address a variety of vaginal sizes but these devices do not adequately differentiate from the traditional balloon occluders from known uterine manipulator technology. Moreover, these devices lack safety stop features to keep the device in proper location for cuff suturing or preclude it from entering fully into the patient's vaginal canal. It also does not address the typical natural anatomic contours of the vaginal vault. Other vaginal occlusive devices have been introduce to address these shortcomings by introducing a head, a shaft and a handle, but these devices lack features that prevent the device from falling out, or other safety or ergonomic features to address various anatomic considerations.

SUMMARY

In accordance with aspects of the present disclosure, a transvaginal occluder includes an elongated housing having proximal and distal portions and an internal cavity defined therebetween, the internal cavity is configured for selective receipt of a surgical instrument therethrough. The elongated housing includes a first material having a first durometer extending between the proximal and distal portions and defining the internal cavity. The first material includes one or more recesses defined therein and extending along the internal cavity. The elongated housing also includes a second material having a second, lower durometer and extending between the proximal and distal portions. The second material is configured to encapsulate a portion of the first material and is configured to engage vaginal tissue. The elongated housing also includes a third material having a third, lowest durometer disposed within the one or more recesses. The third material is configured to engage a shaft of the surgical instrument in a fluid tight manner.

In aspects according to the present disclosure, the second material includes one or more compression regions along a length thereof, the compression region configured to compress during insertion of the transvaginal occluder within a vaginal canal and expand beyond the pelvic floor once inserted therein to fix the transvaginal occluder in vivo. In other aspects according to the present disclosure, the compression region includes surfaces that have angles less than forty-five degrees.

In aspects according to the present disclosure, the third material includes a bulbous section configured to frictionally engage the shaft of the surgical instrument upon insertion thereof. In other aspects according to the present disclosure, the first material includes a taper at a distal portion thereof configured to facilitate insertion of the occluder within the vaginal canal. In yet other aspects according to the present disclosure, the first material includes a flare at a proximal portion thereof configured to facilitate insertion of the surgical instrument therein. In still other aspects according to the present disclosure, the first material includes one or more ribs along a length thereof configured to facilitate retention of the occluder within the vaginal canal.

In accordance with aspects of the present disclosure, a method of making a transvaginal occluder includes printing a housing having proximal and distal portions, the printing including: printing a first material including a first durometer and that is configured to extend between the proximal and distal portions, the first material printed to define an internal cavity therethrough extending between the proximal and distal portions and including one or more recesses defined therein; printing a second material having a second, lower durometer that is configured to extend between the proximal and distal portions, the second material printed to encapsulate a portion of the first material, the second material configured to engage vaginal tissue; and printing a third material having a third, lowest durometer, the third material printed within the one or more recesses of the first material, the third material configured to engage a shaft of a surgical instrument in a fluid tight manner when inserted through the internal cavity.

In aspects according to the present disclosure, the printing includes printing the second material to include one or more compression regions along a length thereof, the compression region configured to compress during insertion of the transvaginal occluder within a vaginal canal and expand beyond a pelvic floor of the vaginal canal once inserted therein to fix the transvaginal occluder in vivo. In other aspects according to the present disclosure, the compression region is printed to include surfaces that include angles less than forty-five degrees.

In aspects according to the present disclosure, the printing includes printing the third material to include a bulbous section configured to frictionally engage the shaft of the surgical instrument upon insertion thereof. In other aspects according to the present disclosure, the printing includes printing the first material to include a taper at a distal portion thereof configured to facilitate insertion of the occluder within a vaginal canal. In yet other aspects according to the present disclosure, the printing includes printing the first material to include a flare at a proximal portion thereof configured to facilitate insertion of the surgical instrument therein. In still other aspects according to the present disclosure, the printing includes printing the first material to include at least one rib along a length thereof configured to facilitate retention of the occluder within a vaginal canal.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the disclosed vaginal occlusive devices are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. Additionally, the term "proximal" refers to the portion of structure that is closer to the clinician and the term "distal" refers to the portion of structure that is farther from the clinician. In the following description, well-known functions or constructions are not described in detail to avoid obscuring this disclosure in unnecessary detail.

In general, this disclosure describes a transvaginal occlusive device for use with various surgical instruments, e.g., uterine manipulators, tenaculums, clamps, forceps, etc. The transvaginal occluder is printed via LAM (liquid additive manufacturing) utilizing different materials (e.g., LSR (liquid silicone rubber)) to create an occluder with different regions of varying durometer to facilitate insertion and use. The occluder includes various geometries such as air cavities and flanges to facilitate insertion, compression and fixation. The occluder is printed utilizing a low durometer material in certain internal regions eliminating the need for internal seals to maintain the integrity of insufflation gases of the vaginal cavity.

FIGS. 1A-3C show one embodiment of a transvaginal occluder for use with various surgical procedures generally referenced as occluder 10. Occluder 10 includes an elongated body 11 having respective proximal and distal portions 12, 14 with an instrument cavity 25 defined therebetween configured to selectively receive a shaft of a surgical instrument "I" therethrough (FIG. 2C). Occluder includes a series of flanges, compression regions and tapered sections configured to facilitate insertion and fixation of the occluder 10 within a vaginal cavity 122 (See FIGS. 3A-3C).

Figure 1A:
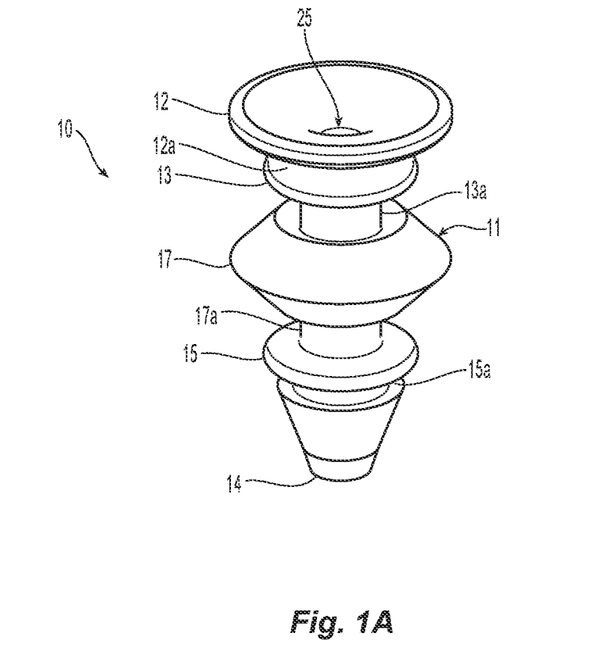
FIG. 1A is a perspective view of one embodiment of a transvaginal occlusion device.
Figure 1B:
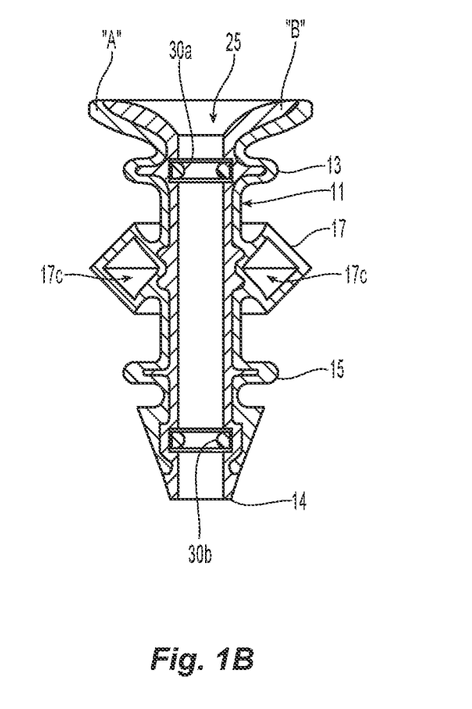
FIG. 1B is a cross section of the transvaginal occluder of FIG. 1A.

More particularly and describing the occluder from proximal portion 12 to distal portion 14, proximal portion 12 is generally rounded and includes a tapered neck 12a extending therefrom that culminates to a proximal flange 13. Proximal flange 13 includes a tapered neck 13a extending therefrom that culminates to a compression region 17 having a hollow cavity 17c defined therein that facilitates compression thereof when induced by an outside force (wall of the vaginal canal 122 during insertion). Compression region 17 transitions to a tapered neck 17a that extends therefrom towards the distal portion 14 and culminates at distal flange 15. Distal flange 15 includes a tapered neck 15a extending therefrom that culminates to distal portion 14. Distal portion 14 is tapered to facilitate insertion into the vaginal canal 122.

Figure 2A:
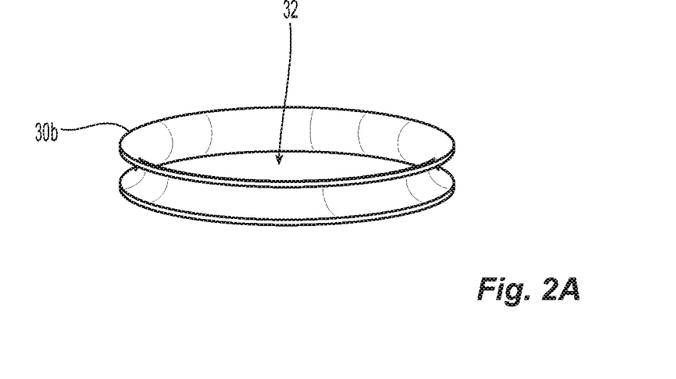
FIG. 2A is an enlarged, perspective view of low durometer material acting as an internal seal of the transvaginal occluder of FIG. 1A.

Instrument cavity 25 extends from the proximal portion 12 to the distal portion 14 and may be sized to accommodate a variety of different surgical instrument shafts "I". The internal periphery of the proximal portion 12 may be flared at a proximal end thereof to facilitate insertion of a surgical instrument (not shown) into the instrument cavity 25. Similar to an instrument seal, the occluder 10 includes one or more areas 30a, 30b made from a low durometer material that are disposed within the cavity 25 and that are configured to frictionally and sealingly engage the instrument shaft "I" during insertion and manipulation thereof to maintain integrity of the insufflated vaginal cavity or pneumoperitoneum during the surgical procedure. FIG. 2A shows one embodiment of a low durometer area 30b for illustrative purposes. As detailed below, the low durometer areas 30a, 30b are constructed or printed during manufacture of the entire occluder 10.

Figure 2B:
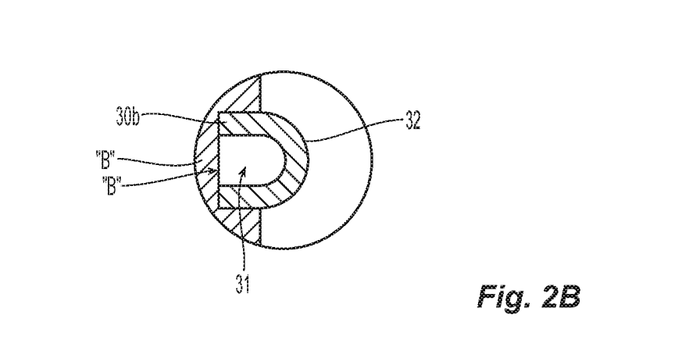
FIG. 2B is a greatly enlarged, cross sectional view of the low durometer material of FIG. 2A shown positioned within a recess defined in a higher durometer material prior to insertion of a surgical instrument.
Figure 2C:
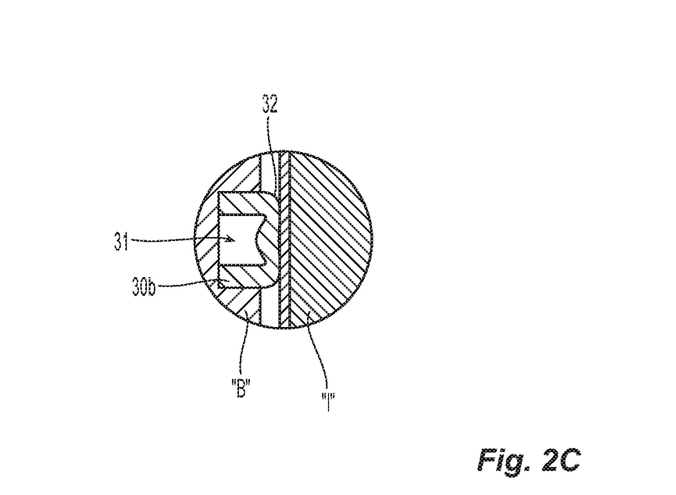
FIG. 2C is a greatly enlarged, cross sectional view of the low durometer material of FIG. 2A positioned within the recess defined in the higher durometer material during insertion of the surgical instrument.

The low durometer areas 30a, 30b include generally bulbous sections, e.g., bulbous section 32, that extend into the cavity 25 for engagement with the instrument shaft "I". The bulbous area 32 includes a hollow cavity 31 defined therein that compresses upon engagement with the instrument shaft "I". The bias of the cavity 31 forces the bulbous area 32 into continuous contact with the instrument shaft "I" during insertion and manipulation thereof.

As best shown in FIG. 1B, the occluder is made from a combination of materials having differing durometers ranging from a high durometer material, e.g., material B", that is configured to provide stiffness to the occluder 10 for insertion and manipulation purposes, to a medium durometer material, e.g., material "A", that is relatively flexible and that is configured to enhance safety and overall comfort of the occluder 10 when positioned in vivo, to a low durometer material, e.g., low durometer areas 30a, 30b, that is configured to facilitate conformation to instrumentation inserted through the occluder 10 to prevent leakage of insufflation gases.

More particularly, the high durometer material, e.g., material "B", may be utilized to provide stiffness to areas such as internal cavity 25 that is configured to receive the instrument "I" therethrough. As such, material "B" is configured to act like a spine of the occluder 10 for insertion and stiffness purposes. The distal portion 14 may include a taper made from material "B" to induce insertion (See FIG. 1B). Material "B" may include areas of varying thickness and geometry to provide increased stiffness to facilitate insertion, manipulation, or retention of the occluder 10. Varying geometries may include any number of projections, ribs, flanges, tapers or reliefs to facilitate insertion, manipulation and/or retention of the occluder 10 inside the vaginal canal 122.

A different material having a medium durometer, e.g., material "A", may be provided on the outside of the occluder 10 to provide some malleability or compressibility to the occluder 10 and provide comfort or safety to the patient during insertion and manipulation. Material "A" may include areas of varying thickness and geometry to provide increased stiffness (albeit less than the durometer of material "B") to facilitate insertion, manipulation, or retention of the occluder 10 or to enhance comfort and safety of the occluder 10, e.g., around areas where the geometry of material "B" may need to be balanced for patient comfort.

Varying geometries may include any number of projections, ribs, flanges, tapers or reliefs to facilitate insertion, manipulation, retention, comfort or safety of the occluder 10 inside the vaginal canal 122. For example, material "A" may be configured to include a compression region 17 having a hollow cavity 17c defined therein that is designed to, upon insertion, compress to allow insertion into the vaginal canal 122 and then expand against the inner peripheral surface of the vaginal canal 122 (vaginal walls) to frictionally retain the occluder 10 in a fixed position for insertion of a surgical instrument "I". The lower durometer (e.g., softness) of material "A" is gentler on the patient and reduces trauma to the vaginal walls. The compression region 17 includes surfaces that are less than forty-five degrees (45°) to facilitate manufacturing as explained below.

As mentioned above, a low durometer material may be utilized within the cavity 25 to create one or more low durometer areas 30a, 30b that are designed to frictionally engage the instrument shaft "I" during insertion and manipulation. These low durometer areas 30a, 30b are configured to maintain engagement with and seal against the instrument shaft "I" to maintain the integrity of the insufflated vaginal canal 122 during the surgical procedure and especially when the uterus is removed. One of more surgical lubricants (not shown) may be utilized with the instrument shaft "I" to ensure a fluid-tight seal with the low durometer areas 30a, 30b.

As shown, material "B" may be manufactured to include one or more recesses "B'" defined therein that are configured to receive and maintain the low durometer areas 30a, 30b in place during insertion and manipulation. Material "B" may also include various mechanical interfaces, e.g., ribs, projections, recesses, configured to mechanically engage areas of material "A" depending upon a specific purpose. Moreover, any of the areas of materials "A" or "B" may be variable along a length thereof for specific purposes, e.g., stiffness, comfort, balance, etc.

Occluder 10 is manufactured using Liquid Additive Manufacturing (LAM) technology which layers liquid silicone rubber (LSR) or the like in varying durometers as the occluder 10 is being printed. The manufacturing technique deposits thin layers of each material (in the range of about 0.2 mm to about 0.35 mm thick) which fully cure one layer at a time to produce a specific part. LSR is a widely used material due to the versatility and unique properties thereof. LSR is non-reactive and stable, as well as resistant to extreme environments and temperatures. LSR is used in industries that span automotive, defense, sporting goods, medical devices and consumer products.

As a result of LAM, the occluder 10 can be printed with the two, three or more varying durometer materials, e.g., material "A", material "B" and the low durometer areas 30a, 30b to form the occluder 10 via a single printing process with no assembly required. As a result, the occluder 10 may be designed with the durometer of the material being determined by the requirements of the specified area, e.g., stiffness, flexibility, comfort, etc. For example, internal seals are not required as the low durometer areas 30a, 30b are simply printed in place during the LAM printing process and the material is designed to engage the surgical instrument shaft "I" in a fluid-tight manner. Moreover, the occluder 10 may be designed such that angles of the various surfaces do not exceed forty-five degrees (45°), which can be an issue with LAM printing technology. As a result, the LAM process allows repeatable and reliable printing without assembly. Further, the LAM process simplifies the formation of collapsible areas, e.g., compression region 17, that are designed to collapse upon insertion and expand to fixate the occluder 10 once properly positioned.

Figure 3A:
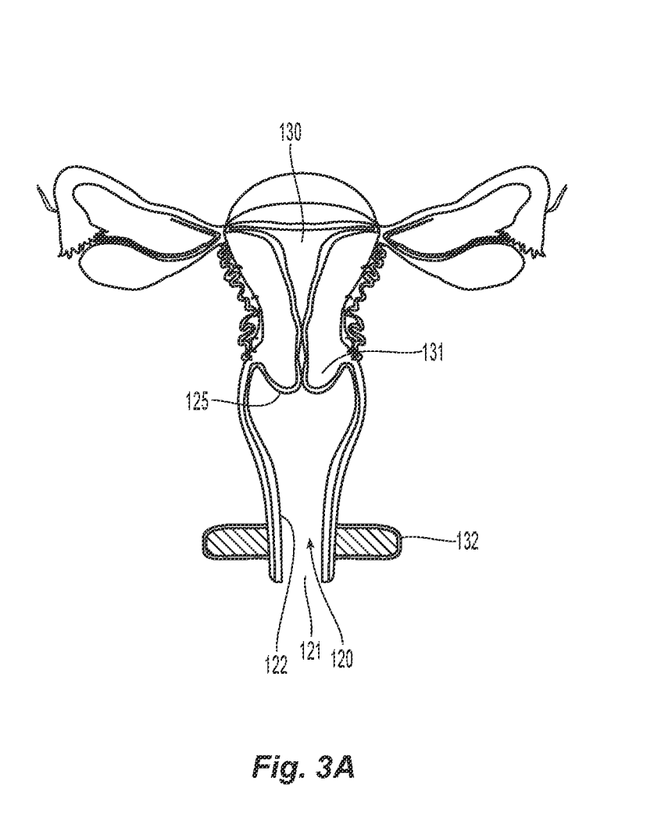
FIG. 3A is schematic, anterior view of a vaginal canal and uterus prior to insertion of the transvaginal occluder.
Figure 3B:
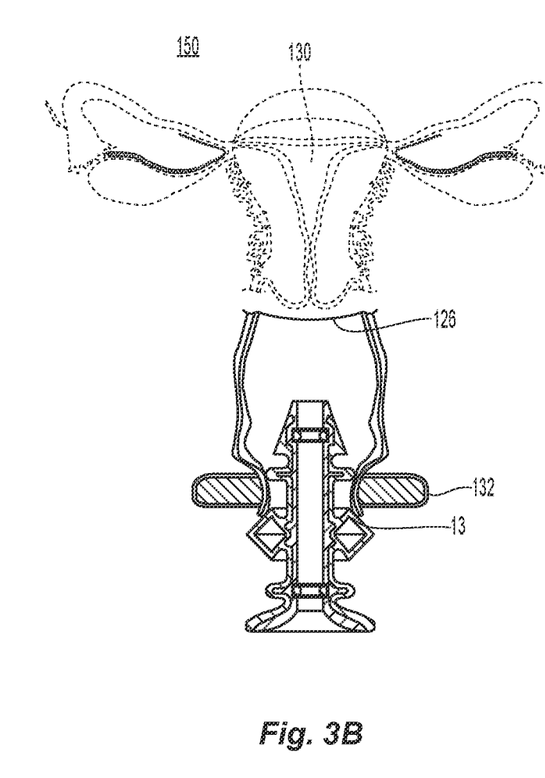
FIG. 3B is a schematic, anterior view of the vaginal canal and uterus (shown in phantom) with the transvaginal occluder of FIG. 1A shown in vivo.

FIG. 3A is a front or anterior view illustrating a vagina 120 having an external vaginal opening 121, followed inwardly to the vaginal canal 122 that extends passed the pelvic floor 132, to the vaginal fornix 125. The uterus 130 (prior to a hysterectomy) is attached to the vaginal fornix 125 at the uterine cervix 131. FIG. 3B is a view similar to FIG. 3A which shows the uterus 130 (now ghosted as being removed) and the vagina 120 with its external vaginal opening 121 and an incised vaginal cuff 126. The occluder 10 is shown within the vaginal canal 122 with the compression region 17 expanded passed the pelvic floor 132 and the flange 13 within the vaginal opening 121 to fix the occluder in place for introduction of surgical instrumentation (not shown).

Figure 3C:
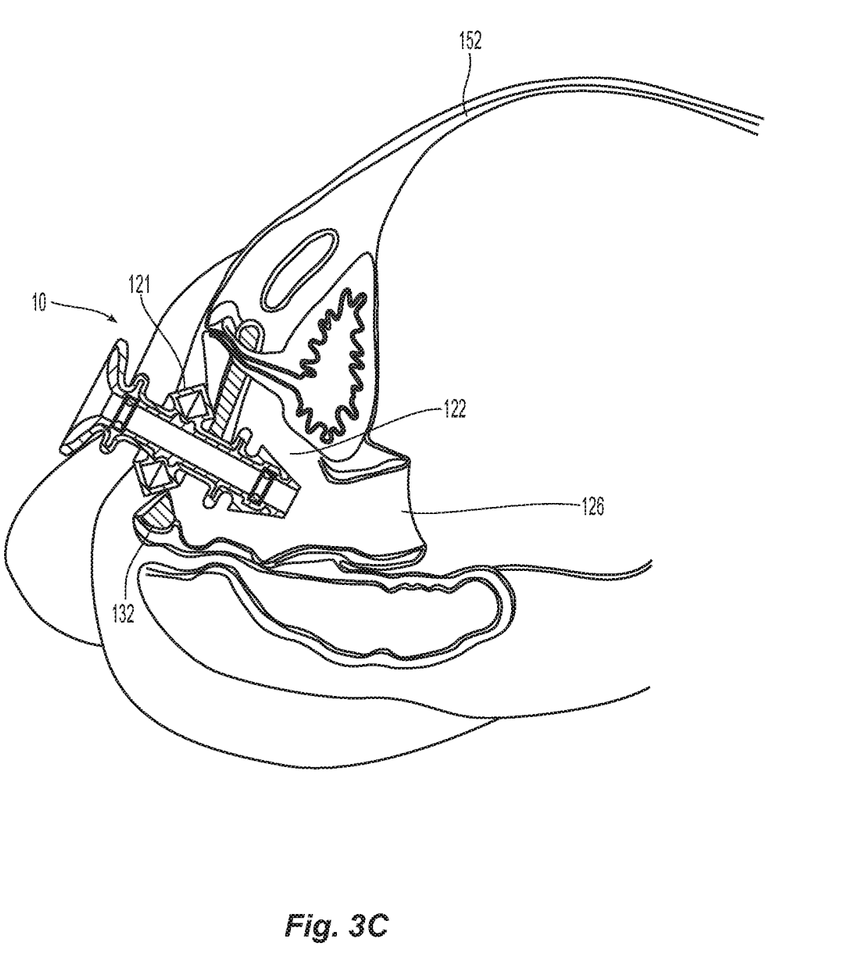
FIG. 3C is schematic, side view of the transvaginal occluder of FIG. 1A shown in vivo.

FIG. 3C shows a side view sectioned along the midline of the pelvis after removal of the uterus 130. The occluder 10 is shown inserted into the vaginal canal 120. Insufflation gas from the abdomen 150 that could otherwise pass through an open vaginal cuff 126 is now prevented from leaking by the occluder 10. A distended anterior abdominal wall 152 highlights the abdomen's increased girth due to a pressurized pneumoperitoneum.

A method of making a transvaginal occluder is also disclosed and includes printing a housing 11 having proximal and distal portions 12, 14. The printing may include an LAM printing process that includes: printing a first material "B" including a first durometer and that is configured to extend between the proximal and distal portions, 12, 14, the first material "B" printed to define an internal cavity 25 therethrough extending between the proximal and distal portions 12, 14 and including one or more recesses "B'" defined therein; printing a second material "A" having a second, lower durometer that is configured to extend between the proximal and distal portions, 12, 14, the second material "A" printed to encapsulate a portion of the first material "B", the second material "A" configured to engage vaginal tissue; and printing a third material, e.g., low durometer areas 30a, 30b, having a third, lowest durometer, the low durometer areas 30a, 30b printed within the one or more recesses "B'" of the first material "B", the low durometer areas 30a, 30b configured to engage a shaft "I" of a surgical instrument in a fluid tight manner when inserted through the internal cavity 25.

The printing may include printing the second material "A" to include one or more compression regions 17 along a length thereof, the compression region configured to compress during insertion of the transvaginal occluder 10 within a vaginal canal 122 and expand beyond a pelvic floor 132 of the vaginal canal 122 once inserted therein to fix the transvaginal occluder 10 in vivo. The compression region may be printed to include surfaces that include angles less than forty-five degrees.

The printing may include printing the third material, e.g., low durometer areas 30a, 30b, to include a bulbous section 32 configured to frictionally engage the shaft of the surgical instrument "I" upon insertion thereof. The printing may include printing the first material "B" to include a taper at a distal portion 14 thereof configured to facilitate insertion of the occluder 10 within a vaginal canal 122. The printing may include printing the first material "B" to include a flare at a proximal portion 12 thereof configured to facilitate insertion of the surgical instrument shaft "I" therein. The printing may include printing the first material "B" to include one or more ribs or flanges, e.g., 13, 15, along a length thereof configured to facilitate retention of the occluder 10 within a vaginal canal 122.

The various embodiments disclosed herein may also be configured to work with robotic surgical systems and what is commonly referred to as "Telesurgery". Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

The invention claimed is:

1. A transvaginal occluder, comprising:
   an elongated housing including proximal and distal portions and an internal cavity defined therebetween configured for selective receipt of a surgical instrument therethrough, the elongated housing including:
      a first material having a first durometer extending between the proximal and distal portions and defining the internal cavity, the first material including at least one recess defined in and extending along the internal cavity;
      a second material having a second, lower durometer and extending between the proximal and distal portions, the second material encapsulating at least a portion of the first material and configured to engage vaginal tissue, wherein the second material includes at least one compression region along a length of the second material, the at least one compression region including a hollow cavity defined in the compression region, the hollow cavity configured to allow the compression region to collapse inwardly during insertion of the transvaginal occluder within a vaginal canal and expand beyond a pelvic floor of the vaginal canal once inserted in the vaginal canal to fix the transvaginal occluder in vivo; and
      a third material having a third, lowest durometer disposed within the at least one recess and configured to engage a shaft of the surgical instrument in a fluid tight manner.

2. The transvaginal occluder of claim 1, wherein the at least one compression region includes surfaces that have angles less than forty-five degrees.

3. The transvaginal occluder of claim 1, wherein the third material includes a bulbous section configured to frictionally engage the shaft of the surgical instrument upon insertion thereof.

4. The transvaginal occluder of claim 1, wherein the first material includes a taper at a distal portion of the first material configured to facilitate insertion of the occluder within a vaginal canal.

5. The transvaginal occluder of claim 1, wherein the first material includes a flare at a proximal portion thereof configured to facilitate insertion of the surgical instrument therein.

6. The transvaginal occluder of claim 1, wherein the first material includes at least one rib along a length along a length of the first material configured to facilitate retention of the occluder within a vaginal canal.

7. A method of making a transvaginal occluder, comprising:
   printing a housing having proximal and distal portions, the printing including:
      printing a first material including a first durometer and extending between the proximal and distal portions, the first material printed to define an internal cavity therethrough extending between the proximal and distal portions and including at least one recess defined in;
      printing a second material having a second, lower durometer and extending between the proximal and distal portions, the second material printed to encapsulate at least a portion of the first material, the second material configured to engage vaginal tissue, wherein the second material includes at least one compression region along a length of the second material the at least one compression region including a hollow cavity defined in the compression region, the hollow cavity configured to allow the compression region to collapse inwardly during insertion of the transvaginal occluder within a vaginal canal and expand beyond a pelvic floor of the vaginal canal once inserted in the vaginal canal to fix the transvaginal occluder in vivo; and
      printing a third material having a third, lowest durometer, the third material printed within the at least one recess and configured to engage a shaft of a surgical instrument in a fluid tight manner when inserted through the internal cavity.

8. The method of making a transvaginal occluder of claim 7, wherein the at least one compression region is printed to include surfaces that include angles less than forty-five degrees.

9. The method of making a transvaginal occluder of claim 7, further comprising printing the third material to include a bulbous section configured to frictionally engage the shaft of the surgical instrument upon insertion thereof.

10. The method of making a transvaginal occluder of claim 7, further comprising printing the first material to include a taper at a distal portion thereof configured to facilitate insertion of the occluder within a vaginal canal.

11. The method of making a transvaginal occluder of claim 7, further comprising printing the first material to include a flare at a proximal portion thereof configured to facilitate insertion of the surgical instrument therein.

12. The method of making a transvaginal occluder of claim 7, further comprising printing the first material to include at least one rib along a length thereof configured to facilitate retention of the occluder within a vaginal canal.

13. A transvaginal occluder, comprising:
   an elongated housing including proximal and distal portions and an internal cavity defined therebetween configured for selective receipt of a surgical instrument through the internal cavity, the elongated housing including:
   a first material having a first durometer extending between the proximal and distal portions, the first material defining the internal cavity and including a recess defined within and extending along the internal cavity;
   a second material having a second, lower durometer configured to encapsulate at least a portion of the first material and configured to engage vaginal tissue upon insertion of the elongated housing into a vaginal canal, wherein the second material includes at least one compression region along a length of the second material, the at least one compression region including a hollow cavity defined in the compression region, the hollow cavity configured to allow the compression region to collapse inwardly during insertion of the transvaginal occluder within a vaginal canal and expand beyond a pelvic floor of the vaginal canal once inserted in to fix the transvaginal occluder in vivo; and
   a third material having a third durometer different from the first and second material, the third material disposed within the recess and configured to engage a shaft of the surgical instrument in a fluid tight manner.

14. The transvaginal occluder of claim 13, wherein the at least one compression region includes surfaces that have angles less than forty-five degrees.

15. The transvaginal occluder of claim 13, wherein the third material includes a bulbous section configured to frictionally engage the shaft of the surgical instrument upon insertion of the surgical instrument within the third material.

16. The transvaginal occluder of claim 13, wherein the first material includes a taper at a distal portion of the first material, the taper configured to facilitate insertion of the occluder within the vaginal canal.

17. The transvaginal occluder of claim 13, wherein the first material includes a flare at a proximal portion of the flare, the flare configured to facilitate insertion of the surgical instrument therein.

18. The transvaginal occluder of claim 13, wherein the first material includes at least one rib along a length of the first material, the at least one rib configured to facilitate retention of the occluder within the vaginal canal.

* * * * *